United States Patent [19]

Nylen et al.

[11] 4,229,542
[45] Oct. 21, 1980

[54] APPARATUS FOR THE MEASURING OF THE CONCENTRATION OF LOW-MOLECULAR COMPOUNDS IN COMPLEX MEDIA

[75] Inventors: Ulf T. G. Nylen; Lars A. G. Qvarnström, both of Lund, Sweden

[73] Assignee: Gambro AB, Sweden

[21] Appl. No.: 755,977

[22] Filed: Dec. 30, 1976

[30] Foreign Application Priority Data

Jan. 2, 1976 [SE] Sweden ............................ 7600024

[51] Int. Cl.² ............................................ C12M 1/34
[52] U.S. Cl. ...................................... 435/291; 435/10
[58] Field of Search ......... 195/127, 103.5 C, 102.5 R; 23/253 R; 210/22, 23, 321 R, 321 B; 435/287, 291, 10, 12, 14; 422/68, 50

[56] References Cited

U.S. PATENT DOCUMENTS

| | | | |
|---|---|---|---|
| 2,797,149 | 6/1957 | Skeggs | 195/127 |
| 2,893,324 | 7/1959 | Isreeli | 103/149 |
| 3,047,367 | 7/1962 | Kessler | 23/230 |
| 3,098,717 | 7/1963 | Ferrari | 23/230 |
| 3,483,990 | 12/1969 | Litle et al. | 210/321 B |
| 3,512,517 | 5/1970 | Kadish et al. | 128/2 |
| 3,721,623 | 3/1973 | Stana | 210/321 R |
| 3,847,809 | 11/1974 | Kopf | 210/321 B |
| 3,902,490 | 9/1975 | Jacobsen et al. | 210/321 B |
| 3,919,051 | 11/1975 | Koch et al. | 195/103.5 R |
| 3,993,560 | 11/1976 | Halpern | 195/127 |
| 4,123,353 | 10/1978 | Hakansson et al. | 210/22 C |

FOREIGN PATENT DOCUMENTS

242177 10/1962 Australia.
162340 of 0000 New Zealand.
219427 3/1968 Sweden.

*Primary Examiner*—Thomas G. Wiseman
*Attorney, Agent, or Firm*—Lerner, David, Littenberg & Samuel

[57] ABSTRACT

A method and apparatus is provided which measures the content of a low-molecular compound, such as glucose, cholesterol, or urea, in a complex medium, such as blood. A dialyzer is placed in contact with the complex medium so that the complex medium may pass therethrough. In addition, dialysis fluid is supplied through the dialyzer to produce a dialysate having a property which can be measured. In the preferred embodiment, an enzyme is added to the dialysate to chemically react with the low-molecular compound to produce a chemical change which can be measured.

17 Claims, 8 Drawing Figures

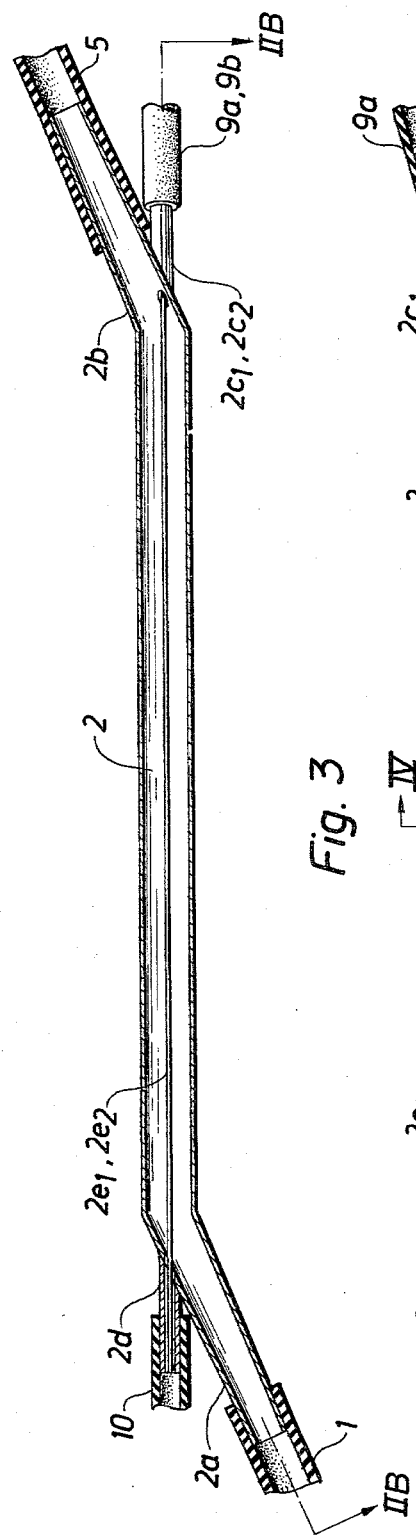
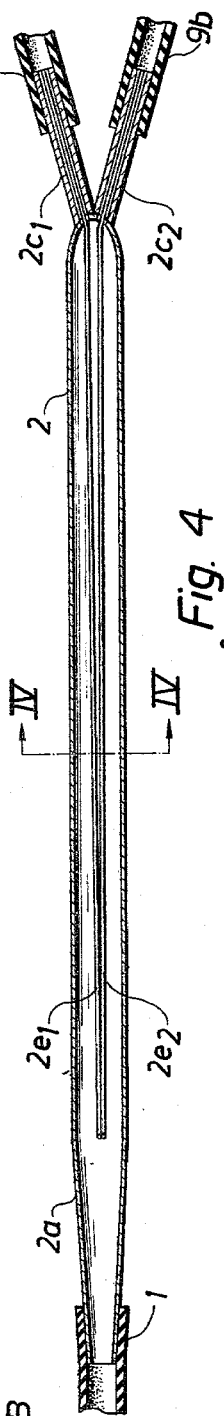
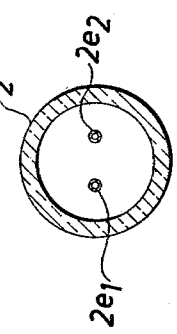
Fig. 2
Fig. 3
Fig. 4

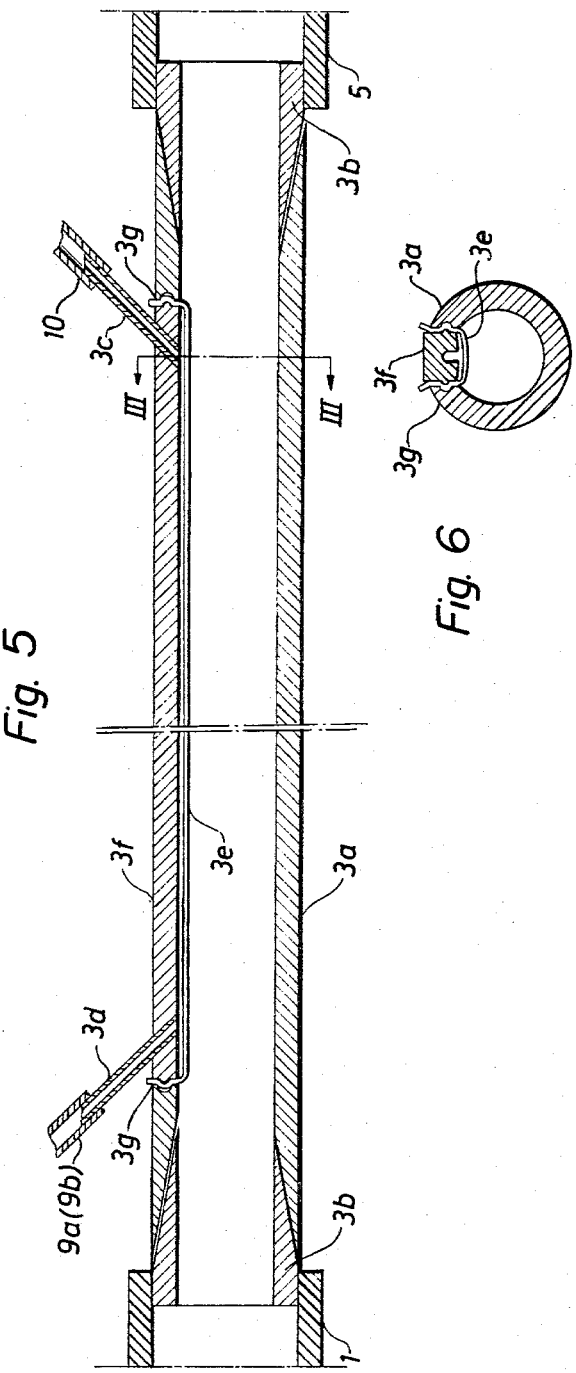

APPARATUS FOR THE MEASURING OF THE CONCENTRATION OF LOW-MOLECULAR COMPOUNDS IN COMPLEX MEDIA

FIELD OF THE INVENTION

The present invention relates to a method for the determination of the concentration of a low-molecular compound in a complex medium, e.g. blood, in particular in connection with medical treatment. The method in accordance with the present invention provides that a small portion of the complex medium is dialysed via a semipermeable membrane whereupon the measurement of the dialysate produced is carried out.

BACKGROUND OF THE INVENTION

It has long been desirable to provide a simple and efficient manner of measuring the content of a low-molecular compound, such as glucose or cholesterol, in a complex medium, such as blood. The present invention has provided such a method and apparatus.

The determination of the concentration of the low-molecular compounds is carried out in connection with chemical reacting the dialysate with an enzyme, e.g. oxidation or hydrolysis, with formation of one or more readily analysable compounds. The measurement can be facilitated in some cases if the dialysate is diluted with a solution of reagent and/or a suitable buffer before the analysis is carried out.

The method in accordance with the invention in the preferred embodiment is intended to be applied to the measurement of glucose concentration in the blood of a patient, whereby the blood can be taken from a patient and introduced into a dialyzer and preferably be returned subsequently to the patient.

In such an applicant the dialyzer used is appropriately a "fibre-kidney" with preferably only one or a small number of fibres around which the blood is connected whilst low-molecular compounds are transmitted to the dialysis fluid passing through, whereby the dialysate is formed which is to be measured. It is appropriate for the dialysis flow through each individual fibre to be controlled separately. As a result the flow through one fibre will be independent of the flow through another fibre. This is achieved appropriately in that each fibre is given a separate inlet and/or separate outlet and is connected to a separate pumping mechanism.

It will be clear to those versed in the art, that the method in accordance with the invention can of course also be applied to quantitative and/or qualitative determinations of low-molecular compounds in complex media other than blood, e.g. in micro-biological cultivating chambers.

In the method described above the low-molecular compounds diffuse over from the complex medium to the dialysis solution in the direction towards a higher pressure. If the dialysis is carried out during a short specified time, the result will be that only a very small part of the low-molecular compounds is removed from the complex medium. The concentration of the low-molecular compounds obtained in the dialysate will be much lower than in the complex medium. The concentration of the low-molecular compounds in the dialysate will, however, in practice be directly proportional to the concentration in the complex medium.

For the measurement of glucose in blood the dialysate is brought into contact with an enzyme, preferably glucose oxidase, appropriately immobilized on a solid matrix, e.g. porous glass. Glucose oxidase catalyzes the oxidation of glucose with consumption of oxygen, formation of hydrogen peroxide and liberation of propones. The difference in the concentration of $O_2$, $H^+$ or $H_2O_2$, which can be easily determined before and after enzymatic reaction respectively by means of suitable electrodes or photometrically using e.g. a pH indicator, thus gives an answer which, owing to the proportionality, directly indicates the concentration of glucose in the complex medium.

The result of the measurement is appropriately calculator-processed directly so that the evaluated result can be used for treatment of the complex medium, e.g. blood, on which the measurement is carried out.

For the measurement of the glucose concentrations the enzyme hexokinase may also be used as an enzyme together with adenosine triphosphate (ATP), when glucose-6-phosphate and adenosine diphosphate (ADP) are formed with simultaneous changes, e.g. generation of heat, which can be measured. Similarly it is quite possible of course to allow the glucose to participate in an electrochemical process, e.g. in a fuel cell with glucose and oxygen as reactants and obtain by this route a quantitative measure of the glucose concentration.

If the method in accordance with the invention is applied to the measurement of penicillin, penicillinase is suitable for use as the enzyme, the change in the pH which occurs being measured.

If the method in accordance with the invention is applied to the measurement of cholesterol, cholesterol oxidase is suitable for use as the enzyme, the change in the concentration of $O_2$ and/or $H_2O_2$ being measured.

If the method in accordance with the invention is applied to the measurement of uric acid, uricase is suitable for use as the enzyme, the change in the value of the pH being measured.

If the method in accordance with the invention is applied to the measurement of urea, urease is suitable for use as the enzyme and the $NH_3$ and/or $NH^{4+}$ formed or the rise in the value of the pH being measured.

If the method in accordance with the invention is applied to the measurement of any kind of substrate for any kind of enzyme, the determination can be carried out in most cases with the help of a thermistor, making use of the change in temperature which almost invariably takes place in enzymatic processes.

The measurement is carried out appropriately with maintaining constant pressure and temperature in the dialyzer, and, if the analysing instrument is sensitive to the same, also at the place of actual measurement.

If a thin dialysis membrane with relatively small pores is chosen, the ultrafiltration of water will be sma. Hence diffusion across the membrane will by and large be decisive. Consequently the dialysis purification is changed so insignificantly in the presence of substantial variations in pressure, that it is not necessary from a practical point of view to keep the pressure constant. It is desirable, however, that the pressure in the dialysis solution should be somewhat higher than in the surrounding complex medium, since the slight ultrafiltration which nevertheless will take place, will reduce the risk of "clotting" of high-molecular substances or cells on the fibre.

In the measurement of glucose concentrations it may be appropriate to dilute the dialysate with a weakly acid solution with the intention of lowering the pH to the pH optimum of the enzyme. If a photometric determination of the glucose concentration is desirable, another enzyme bed containing e.g. immobilized peroxidase may be used for a second enzymatic reaction between hydrogen peroxide and some substrate which gives rise to a colour reaction, e.g. ortho-toluidine. The substrate for this second enzyme stage may, depending upon circumstances, be added before or after the glucose oxidase bed.

The invention also relates to an arrangement for the realization of the above mentioned measurements in complex media. This arrangement is characterized by means for the realization of the dialysis of a small portion of the complex medium, these means comprising one or more lines for the introduction of the dialysis liquid and for the removal of the dialysate obtained, preferably via an enzyme transformation to a measuring unit.

The dialyzer appropriately consists of a fibre dialyzer with preferably one or two hollow semipermeable fibres with separate inlets through which the dialysis liquid is arranged to flow.

In certain cases it is desirable not to remove the complex medium e.g. blood, from its natural surroundings. As an alternative to the said fibre dialyzer, one or more semipermeable fibres provided with flexible tube connections may then be placed directly in the complex medium, e.g. in the blood stream, so as to bring about an intravascular dialysis.

If the membrane material and the flexible tubes are placed directly in the complex medium they should advantageously be treated in such a manner that minimum disturbance is caused in the complex material. When measuring in the blood stream it is appropriate, for example, to use heparinized material.

The arrangement in accordance with the invention appropriately comprises further means for the dilution of the dialysate with water, buffer and/or suitable reagent.

The analysis is made possible in certain cases by connecting in the arrangement in accordance with the invention between the dialyzer and a measuring unit an enzyme bed, e.g. a glass bed with immobilized enzyme for the transformation of the material that is to be measured to compounds which can be measured more readily. The desired enzymatic change can of course also be obtained in that the diluting solution after the dialyzer and/or the dialysis fluid contains the enzyme in free form.

In practice it has been found appropriate to combine the measuring unit with a computer for a direct utilization of the measuring result obtained so as to add the required components to the complex medium, e.g. blood, which is being examined.

In the following the invention will be described in detail with reference to the enclosed drawings which show by may of example preferred embodiments of the arrangement in accordance with the same.

FIG. 1 shows a block diagram of the arrangement.

FIGS. 2, 3, and 4 show three views at right angles to one another of a fibre dialyzer which may form a detail in the arrangement according to FIG. 1.

FIG. 5 shows a plate dialyzer which may form a detail in the arrangement according to FIG. 1.

FIG. 6 shows a section along line III—III in FIG. 5.

Figure 1:
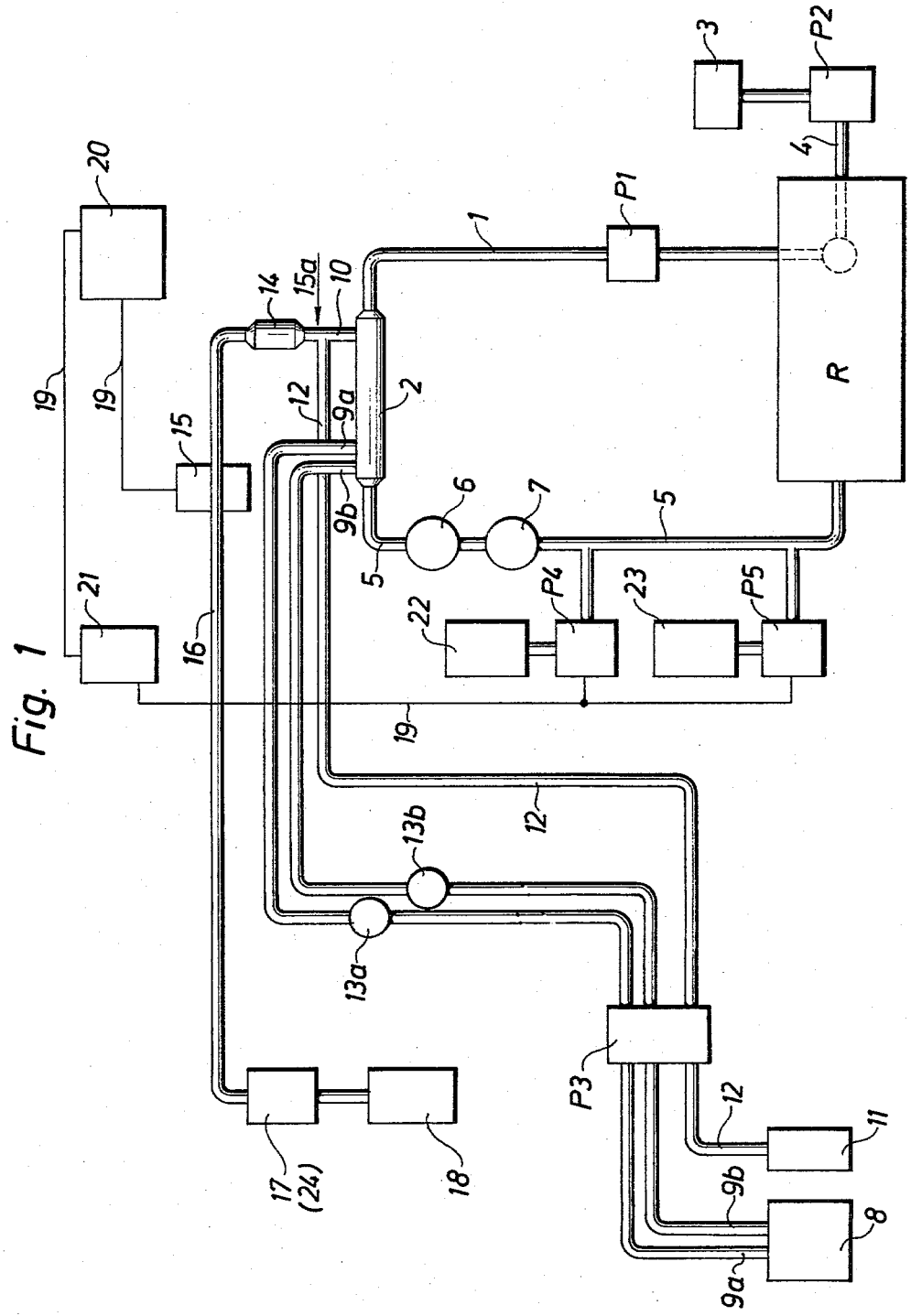
Figure 7:
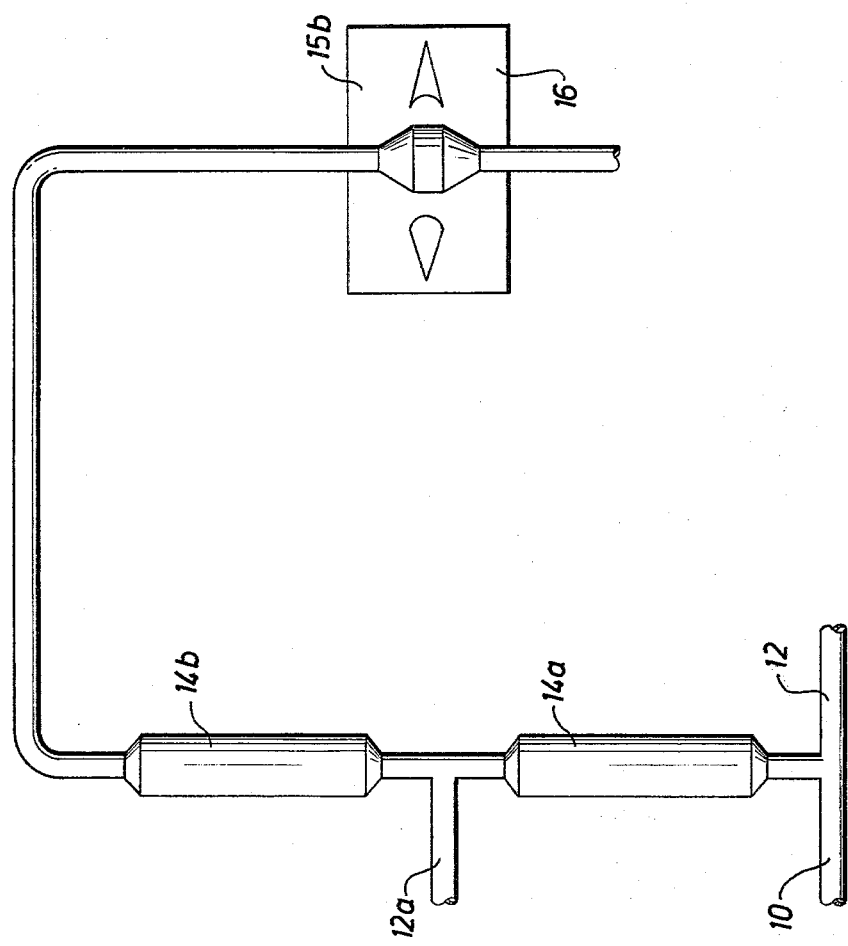
FIG. 7 shows a set of two enzyme beds which may form a detail in FIG. 1.

In FIG. 1 letter R refers to a reservoir for the complex medium which is to be analyzed. The medium is pumped with the help of a pump P via a line 1 to a dialyzer 2. If the medium consists for example of blood, the reservoir R may consist of a human vascular system. In this case it would be appropriate to pump by means of a pump P2 heparin from a reservoir 3 for this material via the lines 4 to a point near the inlet of line 1. In this case this is done so as to prevent coagulation of the blood. The medium under test is then conducted, as can be seen from FIG. 1, via a pressure gauge 6 and a pressure control 7 through a continuation of the line 5 back to the reservoir R.

The dialyzer may, for example, have the form which is shown on a larger scale in FIGS. 2, 3, and 4 or in FIGS. 5 and 6. In FIGS. 2, 3, and 4 the dialyzer consists of a tube 2 to which the line 1 is connected via a tube nozzle $2a$. At the other end of the dialyzer the line 5 for the removal of the examined medium is connected by means of a tube nozzle $2b$. The dialyzer is provided in this case with three tube nozzles, $2c_1$, $2c_2$ and $2d$ which are arranged for the leading in and out respectively of two thin fibres $2e_1$ and $2e_2$ of a semipermeable membrane material, e.g. regenerated cellulose.

Dialysis fluid is conveyed by means of a multi-channel pump P3 from a reservoir 8 through lines $9a$ and $9b$ up to tube nozzles $2c_1$ and $2c_2$. Through these the dialysis fluid is introduced into the fibres $2e_1$ and $2e_2$ to be later discharged via the tube nozzle $2d$ into a line 10. Buffer solution and/or reagent solution is fed directly to this line 10 with the help of the same pump P3 via a line 12. The pressure gauges in the lines $9a$ and $9b$ are designated by $13a$ and $13b$. If differential measurement is required the diluted dialysate is then passed via a measuring point $15a$ and further through a unit 14 containing immobilized enzyme to a measuring point 15, e.g. a measuring electrode or a photometer, and further through a line 16 via a flowmeter 17 or a drop chamber 24 with drop counter for checking the rate of flow, and down to a drainage vessel 18. In FIG. 1 there is shown a general flowmeter 17 as well as a drop chamber 24. Naturally one of the two may be omitted.

The result obtained by means of e.g. measuring electrode or photocell 15 is passed via a line 19 and the measuring unit proper 20 to a computer 21. This computer may be arranged to control the pumps P4 and P5 for the pumping of a fluid from the reservoirs 22 and 23 directly to the line 5 for direct action upon the medium which is being examined. If it is e.g. a question of measurement of glucose in the blood of a patient the reservoir 22 may contain insulin and the reservoir 23 may contain glucose and/or glucagon.

In FIGS. 5 and 6, another embodiment of the dialyzer is shown and includes a tube $3a$ to which the line 1 is connected via a tube nozzle $3b$. The other end of the dialyzer is connected via another tube nozzle $3b$ to the line 5 for the removal of the examined medium. The dialyzer in this case is provided further with two or more tube nozzles $3c$ and $3d$ which are arranged to introduce and to discharge, respectively, dialysis fluid under the semipermeable membrane which is designated $3e$.

For practical reasons the tube nozzles $3c$ and $3d$ have been shaped into a loose, coverlike part $3f$ which, with the help of a locking device $3g$, is also used for clamping down the membrane $3e$.

Figure 8:
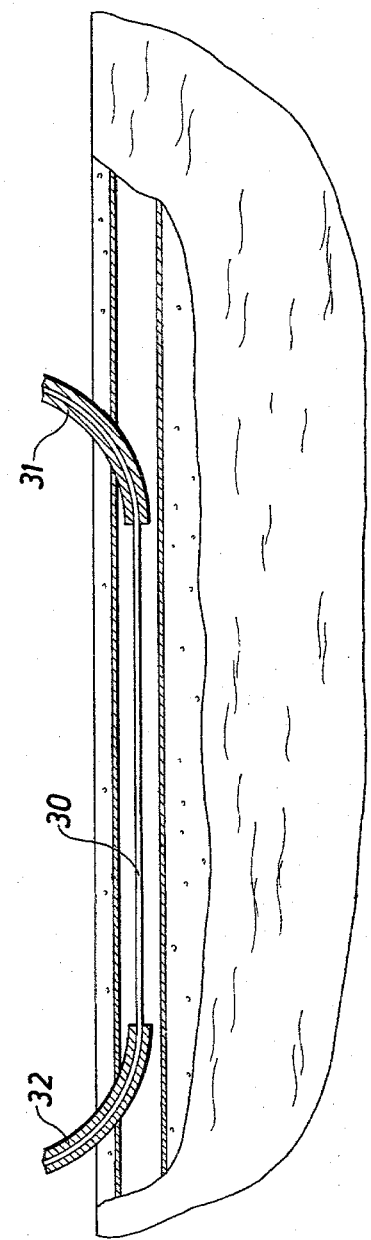
FIG. 8 shows the dialysis process and the principle of intravascular dialysis.

In FIG. 8 there is shown how the enzyme unit can be made up of two enzyme beds arranged in series and connected to the line 10 from the dialyzer 2 and to the line 12 for diluting fluid etc. The numeral 12a indicates an alternative point of dilution between the two enzyme beds. This system may be used for bringing about and measuring a colour change and it is connected to a photometer 15b. The dialysate then passes via the line 16 to a possible flowmeter and further to the drainage vessel 18 shown in FIG. 1.

In FIG. 9 there finally is shown how the dialysis may be carried out directly in a blood vessel, in that a hollow fibre 30 of a semipermeable membrane material is led in and out via the leading tubes 31 and 32. Through these leading tubes the fibre is connected subsequently to lines corresponding to the lines 9a (or 9b) and 10 in FIG. 1, so that dialysis fluid can be made to pass through it in the same manner as through the fibres in dialyzer 2 in FIG. 1.

Naturally the invention is not confined solely to the embodiment described above, but may be varied within the framework of the following claims. For example, two or more of the above mentioned pumps may be co-ordinated in that, for example, one tube pump is made to act upon two or more flexible tubes.

The arrangement in accordance with the invention is particularly suitable in the medical treatment of a diabetic patient and can then serve as a so-called artificial pancreas. For those versed in the art it is clear, however, that the arrangement in accordance with the invention can also be used for the measurement and/or control of complex media other than blood.

We claim:

1. Apparatus for sampling and measuring the content of a low-molecular weight compound in a complex fluid medium to be sampled, comprising:
    a dialyzer having one or more semipermeable membranes having inlet and outlet means to be disposed within said complex fluid medium to form therein one or more passageways for the passage of dialysis fluid, said passageways being substantially smaller in volume than the volume of said complex fluid medium surrounding said passageways for dialyzing only a fractional portion of said complex fluid medium,
    means for supplying said dialysis fluid through said passageways in said complex fluid medium such that only a fractional portion of said surrounding complex fluid medium is acted on by said dialysis fluid and dialyzed whereby a fractional portion of the low-molecular weight compound diffuses into said passageways containing said dialysis fluid to produce a dialysate in said passageways,
    means for maintaining the pressure of said dialysis fluid within said passageways higher than the pressure of said complex fluid medium to substantially reduce ultrafiltration from said complex fluid medium to said dialysis fluid, a reaction zone connected to said passageways including means for supplying enzyme under conditions sufficient for the enzyme to react with the dialysate, and
    means connected to said reaction zone for measuring a property of said enzymatically reacted dialysate.

2. The apparatus of claim 1 wherein said dialyzer includes two hollow fibres of a semipermeable membrane material through which said dialysis fluid flows and which receives by diffusion said low-molecular weight compound which combines with said dialysis fluid to produce said dialysate.

3. The apparatus of claim 2 further including means for separately controlling the flow of dialysis fluid through each of said two hollow fibers.

4. The apparatus of claim 1, wherein said semipermeable membranes are hollow fibres.

5. The apparatus of claim 1, wherein said pressure means includes a pumping mechanism for pumping said dialysis fluid through said passageways.

6. The apparatus of claim 1 wherein a portion of said dialyzer, through which dialysis fluid passes, is placed directly in the source of the complex medium.

7. The apparatus of claim 1 wherein said dialyzer includes one or more hollow fibres of a semipermeable membrane material through which said dialysis fluid flows and which receives by diffusion said low-molecular weight compound which combines with said dialysis fluid to produce said dialysate.

8. The apparatus of claim 7 wherein said hollow fibres are made of regenerated cellulose.

9. Apparatus in accordance with claim 1 wherein said dialyzer is a plate dialyzer including a membrane which is arranged in said dialyzer to form chambers through which the dialysis fluid can be pumped.

10. Apparatus in accordance with claim 9 wherein said membrane is fixed by means of a clamping arrangement to the walls of said dialyzer to form said chambers.

11. Apparatus in accordance with claim 1 further including means for diluting said dialysate with water, buffer, and/or reagent solution.

12. Apparatus in accordance with claim 1 wherein said reaction zone includes one or more enzyme beds of immobilised enzyme connected between said dialyzer and said measuring means.

13. Apparatus in accordance with claim 1 further including a computer unit connected to said measuring means for the evaluation of said measuring result which may be utilized for the treatment of said complex medium.

14. Apparatus in accordance with claim 1 further including a flowmeter for controlling the flow through said measuring means.

15. Apparatus in accordance with claim 11 wherein said measuring means include electrodes.

16. Apparatus in accordance with claim 1 wherein said measuring means includes thermistors.

17. The apparatus of claim 1 wherein said complex medium is blood and said compound is glucose.

* * * * *